(12) United States Patent
Kim et al.

(10) Patent No.: US 9,513,217 B2
(45) Date of Patent: Dec. 6, 2016

(54) NON-INVASIVE METHOD AND APPARATUS FOR SCREENING HIGH-QUALITY SEEDS

(75) Inventors: Jeehyun Kim, Daegu (KR);
 Hee-Young Jung, Daegu (KR);
 Changho Lee, Daegu (KR);
 Seung-Yeol Lee, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 238 days.

(21) Appl. No.: 13/640,663

(22) PCT Filed: Mar. 8, 2011

(86) PCT No.: PCT/KR2011/001576
 § 371 (c)(1),
 (2), (4) Date: Nov. 21, 2012

(87) PCT Pub. No.: WO2011/129526
 PCT Pub. Date: Oct. 20, 2011

(65) Prior Publication Data
 US 2013/0057871 A1 Mar. 7, 2013

(30) Foreign Application Priority Data
 Apr. 13, 2010 (KR) .................. 10-2010-0033889

(51) Int. Cl.
 *G01N 21/47* (2006.01)
(52) U.S. Cl.
 CPC ................ *G01N 21/4795* (2013.01)
(58) Field of Classification Search
 CPC ............................................. G01N 21/4795
 (Continued)

(56) References Cited

U.S. PATENT DOCUMENTS 6,293,674 B1 * 9/2001 Huang et al. ............... 351/221
7,242,480 B2 * 7/2007 Alphonse ................... 356/479
(Continued)

FOREIGN PATENT DOCUMENTS

JP 2008512686 A 4/2008
JP 2009-131666 A 6/2009
(Continued)

*Primary Examiner* — Tarifur Chowdhury
*Assistant Examiner* — Omar Nixon
(74) *Attorney, Agent, or Firm* — Reinhart Boerner Van Deuren P.C.

(57) ABSTRACT

Disclosed is a method and apparatus for the non-invasive selection of high-quality seeds, based on optical coherence tomography, by which pathogen-infected and pathogen-free seeds can be discriminated in a non-invasive manner. The apparatus is operated by the processes of scanning a seed of diagnostic interest in a non-invasive manner using an optical coherence tomographic unit; processing interference signals of the scanned tomographic images to produce tomographic image data of the seed of diagnostic interest; analyzing the tomographic image data; comparing the analyzed tomographic image data with preset reference tomographic image data; diagnosing the seed of diagnostic interest as a pathogen-infected or pathogen-free seed according to the comparison data; and selecting high-quality seeds according to the diagnosis data. It can screen high-quality seeds with rapidity, convenience, and accuracy at a low cost and is industrially applicable, making a great contribution to agricultural quarantine inspection.

8 Claims, 4 Drawing Sheets

(58) Field of Classification Search
USPC .......................................................... 356/479
See application file for complete search history.

(56) References Cited

U.S. PATENT DOCUMENTS

2006/0112628 A1* 6/2006 Kotyk et al. .............. 47/58.1 SE
2009/0027689 A1* 1/2009 Yun et al. ..................... 356/511

FOREIGN PATENT DOCUMENTS

| KR | 1020030019863 A | 3/2003 |
| KR | 1020060003739 A | 1/2006 |
| WO | WO 2006/039091 A2 | 4/2006 |
| WO | WO 2010/000266 A1 | 1/2010 |

* cited by examiner

NON-INVASIVE METHOD AND APPARATUS FOR SCREENING HIGH-QUALITY SEEDS

TECHNICAL FIELD

The present invention relates to a method and apparatus for screening high-quality seeds in a non-invasive manner. More particularly, the present invention relates to a method and apparatus for the non-invasive selection of high-quality seeds by which pathogen-free and pathogen-infected seeds can be discriminated in a non-invasive manner.

BACKGROUND ART

Selection of high-quality seeds is an important technique in agriculture. Criteria for high-quality seeds include external and internal factors. With regard to a morphological aspect, high-quality seeds are those that must be free of contamination, deformation, and discoloration. In addition, they should be large and heavy and have a fresh flavor characteristic of themselves. As to the internal factors, they include genetic homogeneity, strong germinative power, and lack of intrinsic diseases.

Most of the currently distributed seeds in South Korea come from foreign countries, mainly South-East Asia. After being imported, seeds are distributed to domestic farmers or exported to third countries. Such seed gathering from abroad are advantageous in terms of production cost, seed gathering environment, and quality, but is always associated with the problem of the inflow of diseases and insect pests unfamiliar in the domestic environment. In South Korea, clearance permission of seeds to be exported or imported is determined not by separate culturing, but by inspection at the scene or laboratory examination. The quantity of seeds which cannot pass the customs because of the detection of intrinsic diseases increases every year. Such inspection of intrinsic diseases is conducted on some of the subject seeds, i.e., a trace number of the subject seeds, due to problems associated with time, labor, and cost.

However, since pathogens are, for the most part, present at a very low density in seeds, inspection must be made on as many seed samples as possible. Practically, it is impossible to make a full inspection with conventional methods due to complex procedure, time, labor, and cost. Thus, there is a need for a novel selection method.

After seeds that are of quality in appearance are gathered for importation, they are examined for intrinsic diseases by quarantine inspection in most countries of the world. In addition, seed companies and agricultural offices select high-quality seeds before seed distribution.

Currently, the selection of high-quality seeds resorts mostly to the naked eye. Also typically used are selection techniques include selection by specific gravity using brine assortment, by weight using an electric fan, and by volume using sieves. In addition, seeds are sowed in soil or media to examine the presence of foreign seeds, germinative power, and intrinsic diseases. As such, conventional selection methods suffer from the disadvantage of being poor in accuracy or requiring extensive time and labor because they are directed toward appearance properties or seed sowing.

Turning to intrinsic diseases of seeds, high-quality seeds are difficult to select with conventional methods. Their inspection spectrum is limited to some pathogenic fungi and viruses. In addition, expensive inspection instrument, extensive labor, much expense, and skilled experts are often beyond the capacity of small and medium-sized companies and offices that are not financially supported.

DISCLOSURE

Technical Problem

Accordingly, the present invention has been made keeping in mind the above problems occurring in the prior art, and an object of the present invention is to provide an apparatus and a method for the non-invasive selection of high-quality seeds, based on optical coherence tomography, by which pathogen-infected and pathogen-free seeds can be discriminated in a non-invasive manner with rapidity, convenience, and accuracy at a low cost.

Technical Solution

In accordance with an aspect thereof, the present invention provides an apparatus for non-invasive selection of high-quality seeds, comprising: an optical tomographic unit for scanning seeds of diagnostic interest in a non-invasive manner to produce a tomographic image and generating an interference signal of the tomographic image; a signal processor for processing the interference signal generated from the optical tomographic unit to generate tomographic image data of the seeds of diagnostic interest; a diagnostic unit for determining whether the seeds of diagnostic interest are pathogen-infected seeds or pathogen-free seeds by analyzing the tomographic image data generated by the signal processor and comparing the analyzed data with preset reference tomographic image data, and for generating diagnosis data; and a selection unit for discriminating pathogen-infected and pathogen-free seeds according to the diagnosis data to select high-quality seeds.

In accordance with another aspect thereof, the present invention provides a method for non-invasive selection of high-quality seeds, comprising: scanning a seed of diagnostic interest in a non-invasive manner using an optical coherence tomographic unit; processing interference signals of the scanned tomographic images to produce tomographic image data of the seed of diagnostic interest; analyzing the tomographic image data; comparing the analyzed tomographic image data with preset reference tomographic image data; diagnosing the seed of diagnostic interest as a pathogen-infected or pathogen-free seed according to the comparison data; and selecting high-quality seeds according to the diagnosis data.

Advantageous Effects

Based on optical coherence tomography, the present invention can discriminate pathogen-infected and pathogen-free seeds in a non-invasive manner on a mass scale and thus can screen high-quality seeds with rapidity, convenience, and accuracy at a low cost. Therefore, the present invention is applicable to agricultural quarantine inspection.

In addition, the present invention can be automated and does not require skilled experts, but only inspection instruments. Therefore, the present invention allows the full inspection of seeds at low cost. Moreover, utilizing the histological modification induced by pathogenic infection, the present invention can detect a pathogen even if it is present at a very low density.

MODE FOR INVENTION

Figure 1:
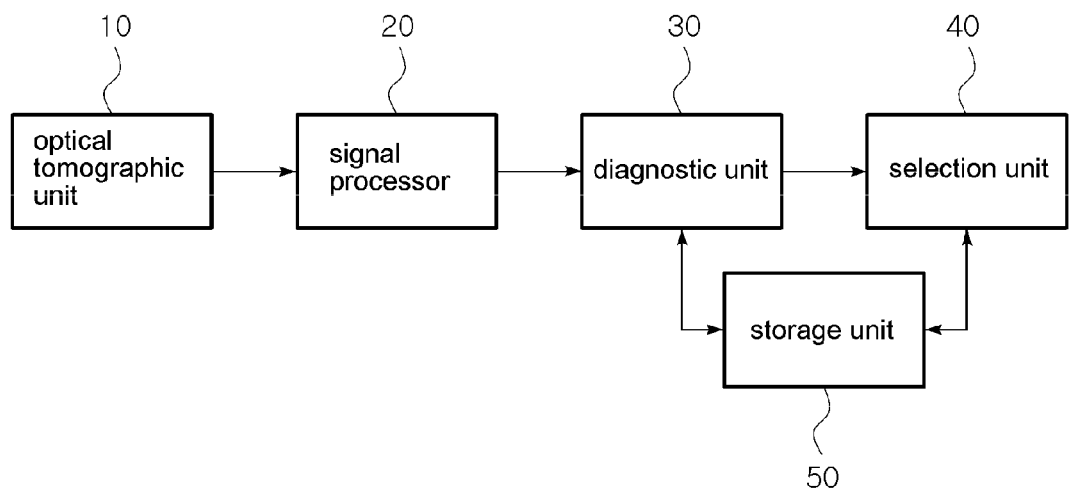
FIG. 1 is a schematic block diagram showing a structure of the apparatus for the non-invasive selection of high-quality seeds according to the present invention.

Below, a description will be given of preferred embodiments of the present invention in conjunction with the accompanying drawings. It should be apparent to those skilled in the art that although many specified elements such as concrete components are elucidated in the following description, they are intended to aid the general understanding of the invention and the present invention can be implemented without the specified elements. Further, in the description of the present invention, when it is determined that the detailed description of the related art would obscure the gist of the present invention, the description thereof will be omitted.

Throughout the accompanying drawings, the same reference numerals are used to designate the same or similar components.

Unless the context clearly demands otherwise, throughout the description and the claims, the term "connected to" is intended to encompass the situation of "connected indirectly to through an element" as well as "connected directly to." Unless the context clearly requires otherwise, throughout the description and the claims, the words "comprise," "comprising," and the like are to be construed in an inclusive sense as opposed to an exclusive or exhaustive sense, that is to say, in the sense of "including, but not limited to."

In embodiments of the present invention, optical coherence tomography is utilized to select high-quality seeds in a non-invasive manner. To begin with, the structure of an apparatus for the non-invasive selection of high-quality seeds based on optical coherence tomography will be described in detail with reference to the drawings.

With reference to FIG. 1, an apparatus for the non-invasive selection of high-quality seeds according to the present invention is structurally depicted in a block diagram.

As shown in FIG. 1, the apparatus for the non-invasive selection of high-quality seeds according to the present invention comprises an optical coherence tomographic unit 10, a signal processor 20, a diagnostic unit 30, a selection unit 40, and a storage unit 50. The diagnostic unit 30, the selection unit 40, and the storage unit 50 may be integrated into a personal computer (PC) or a programmed control system.

The optical coherence tomographic unit 10 is adapted to take tomographic images from seeds of diagnostic interest in a non-invasive manner without dissection, and is used herein to irradiate seeds with light from a broadband light source to generate interference signals mediated by a Michelson interferometer from which the tomographic images of the seeds can be configured. In more detail, the optical coherence tomographic unit 10 works on the basis of OCT (optical coherence tomography). So long as it is OCT, any OCT, such as time-domain OCT, spectral-domain OCT, swept source OCT, etc. may be employed in the present invention.

The signal processor 20 is designed to process the interference signals generated from the optical coherence tomographic unit 10 to produce tomographic image data of the seed of diagnostic interest. In greater detail, the signal processor 20 outputs tomographic image data after performing DC filtering, envelope detection, and digital conversion.

The diagnostic unit 30 functions to analyze the tomographic structures of the seeds of diagnostic interest through the tomographic image data supplied from the signal processor 20. The diagnostic unit 30 retrieves tomographic data stored as a reference image from the storage unit 50 and compares a tomographic data obtained from the analysis of the seeds of diagnostic interest with the reference image data. The seeds are diagnosed as being pathogen-infected if the images are not coincident with each other and as being pathogen free if the images are coincident with each other. The diagnosis data is transmitted to the selection unit 40. In another preferred embodiment of the present invention, the diagnostic unit 30 diagnoses the seeds of diagnostic interest as pathogen-infected seeds if there is a layer in the analyzed tomographic structure and as pathogen-free seeds if there is no layer in the analyzed tomographic structure. The diagnosis of the diagnostic unit 30 may be implemented by operating a diagnosis program installed on a personal computer (PC).

Depending on the diagnosis data transmitted from the diagnostic unit 30, the selection unit 40 works to sort seeds of diagnostic interest. For example, the selection unit 40 is connected to a separate device for selecting seeds, and orders the device to advance pathogen-infected and pathogen-free seeds into different respective lines or to sort only pathogen-infected seeds separately according to the diagnosis data.

The storage unit 50 stores tomographic image data that are preset as a reference to be used for comparison with tomographic image data in the diagnostic unit 30, diagnosis data, and various data necessary for selecting high-quality seeds.

Figure 2:
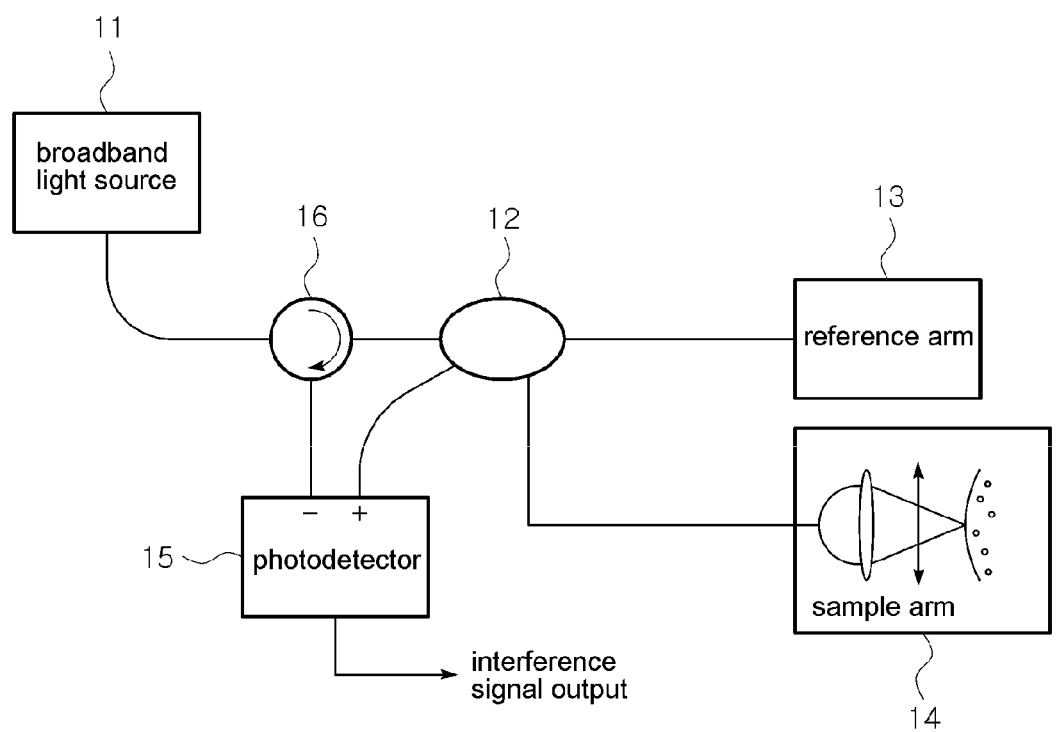
FIG. 2 is a schematic block diagram showing a structure of an optical coherence tomographic unit in the apparatus for the non-invasive selection of high-quality seeds according to the present invention.

With reference to FIG. 2, a detailed description is given of the optical coherence photographic unit 10.

As shown in FIG. 2, the optical coherence tomographic unit 10 comprises a broadband light source 11, a photocoupler 12, a reference arm 13, a sample arm 14, a photodetector 15, and optionally an optical circulator 16. There are connections formed among the broadband light source 11, the photocoupler 12, the reference arm 13, the sample arm 14, the photodetector 15, and optionally the optical circulator 16 via optical fiber.

The broadband light source 11 generates a broad band of light for tomography purposes. In one embodiment of the present invention, the broadband light source 11 may be an SLED (super luminescence emitting diode) centered at 1310 nm with a full length at half maximum of 150 nm.

The photocoupler 12 functions to split the coincident light into two light beams which are directed to the reference arm 13 and the sample arm 14, respectively, and to inversely couple the two reflected beams coincident from the reference arm 13 and the sample arm 14 and transmit the coupled light beams to the photodetector 15.

When light is coincident from the photocoupler 12 on the reference arm 12, the arm 12 reflects the light, as it is, to the photocoupler 12. In accordance with one embodiment of the present invention, the reference arm 13 is embodied by an RSOD (Rapidly Scanning Optical Delayline) which provides a variable optical path length. The RSOD consists of a diffraction grating with 600 grooves/mm and a galvo-scanner for changing the path length at 300 Hz.

The sample arm 14 is adapted to focus the light coming from the photocoupler 12 which strikes a seed of diagnostic interest and to transmit the backscattered light from the seed back into the photocoupler 12. The galvo-scanner in the sample arm 12 is used to generate the B-mode scan. In the sample arm 12, the light is focused by an objective lens with a 15 mm focal length. The B-scanning range is 2 mm.

The photodetector 15 detects interference signals coincident from the photocoupler 12 in which backscattered light from the reference arm 13 and the sample arm 14 of the Michelson interferometer are coupled, and converts the signal to an electrical signal (voltage). Interference signals of the two backscattered light beams from the reference arm 13 and the sample arm 14 are observed by the photodetector 15 when the path length between the reference arm 13 and the sample arm 14 (the optical path length) matches the coherence length of the source.

According to one preferred embodiment of the present invention, the photodetector 15 may be a balanced photodetector. In this case, the apparatus of the present invention further comprises an optical circulator 16 that redirects the light that was redirected back to the broadband light source 11 from the photocoupler 12 towards a negative input terminal of the photodetector 15. In this construction, the photodetector 15 increases the signal-to-noise ratio of the interference signal that was detected.

In the optical coherence tomographic unit 10, the light generated from the broadband light source 11 is split into two beams by the photocoupler 12 which are coincident on the reference arm 13 and the sample arm 14, respectively. The light coincident on the reference arm 13 is reflected by a reference mirror (not shown), while the light coincident on the sample arm 14 is reflected by interfaces of the seed of diagnostic interest. These backscattered light beams are directed backwards into the photocoupler 12.

When the two backscattered light beams from the reference arm 13 and the sample 14 are coupled back to the photocoupler 12, a difference between reflection coefficients of the two backscattered beams produces an interference signal.

The interference signal is detected by the photodetector 15 and converted into an electric signal.

Two- or three-dimensional images of the seed of diagnostic interest can be obtained by measuring interference signals generated when the focal position of the focusing lens (not shown) in the sample arm 14 is moved in a lateral direction along the surface of the seed while changing the distance between a collimating lens (not shown) and a reference mirror (not shown) in the reference 13.

The use of the apparatus for the non-invasive selection of high-quality seeds on the basis of optical coherence tomography in screening high-quality seeds in a non-invasive manner will be understood from the following description with reference to the drawings.

Figure 3:
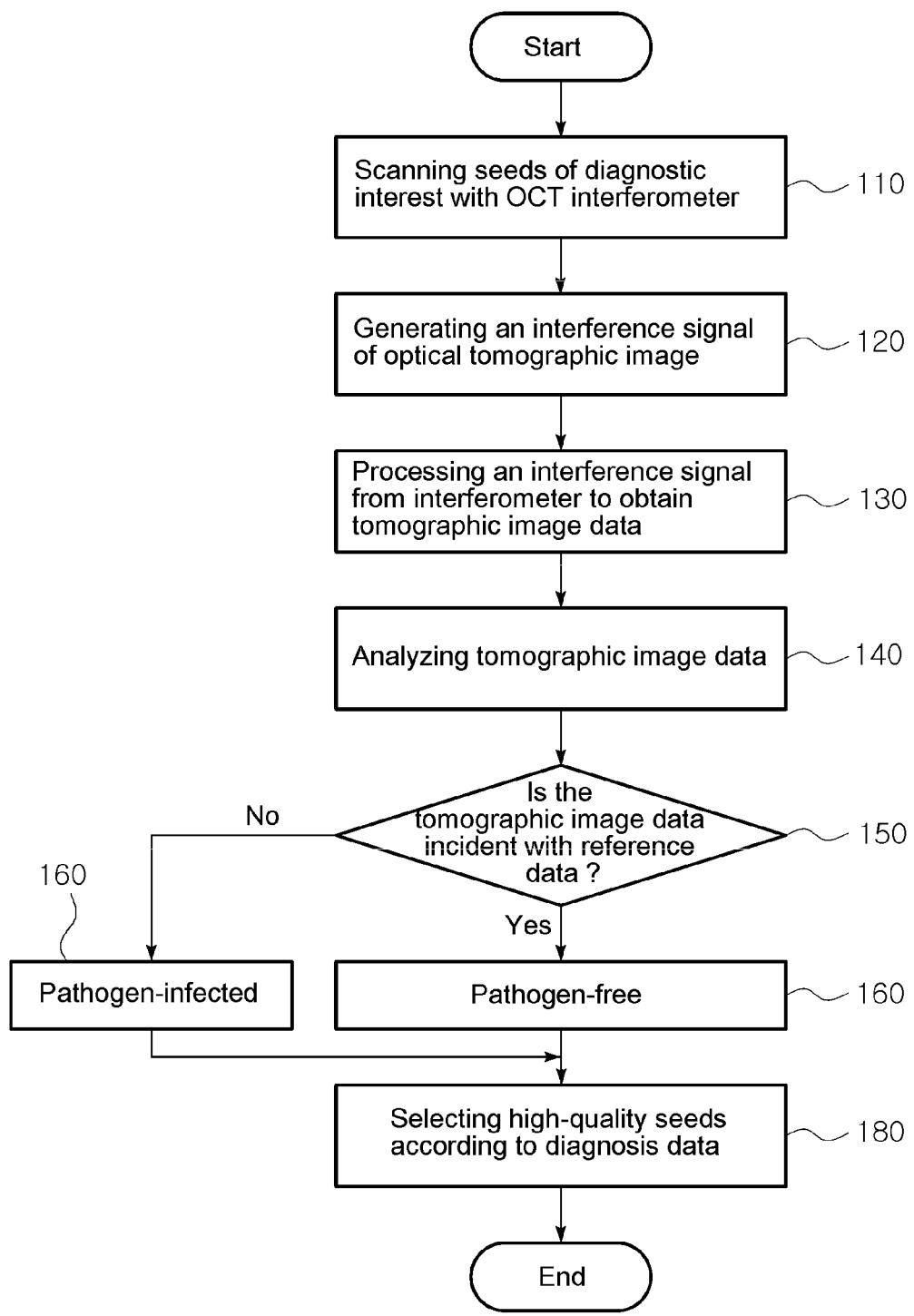
FIG. 3 is a flowchart showing a method for the non-invasive selection of high-quality seeds according to the present invention.

FIG. 3 is a flowchart illustrating a method for selecting high-quality seeds in a non-invasive manner in accordance with another aspect of the present invention.

As shown in FIG. 3, the method for the non-invasive selection of high-quality seeds starts with scanning a seed of interest in a non-invasive manner using optical coherence tomographic unit 10 (S110). Then, interference signals of the optical coherence tomographic images obtained are transmitted to the signal processor 20 (S120). Next, the signal processor 20 processes the interference signals generated from the optical coherence tomographic unit 10 to produce tomographic image data of the seed of diagnostic interest (S130).

The diagnostic unit 30 receives the tomographic image data from the signal processor 20 and analyzes it (S140). Afterwards, the apparatus for the non-invasive selection of high-quality seeds compares the tomographic image data analyzed by the diagnostic unit 30 with preset reference tomographic image data (S150).

Figure 4:
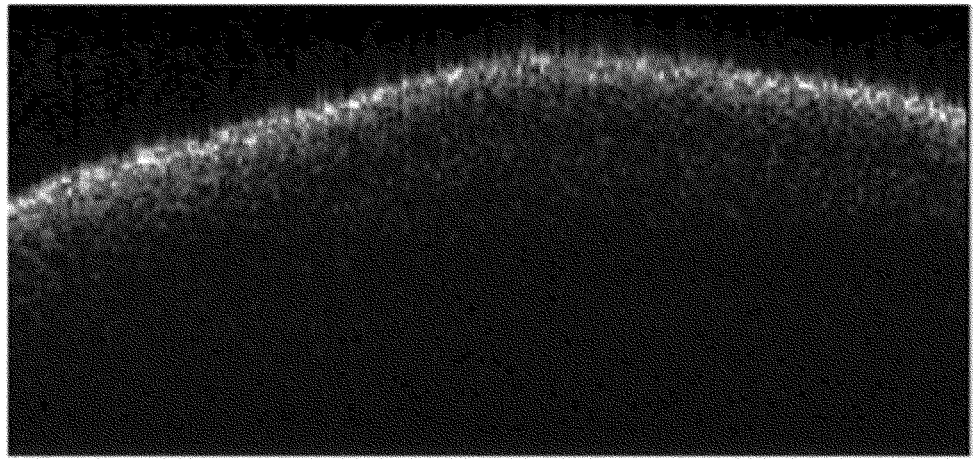
FIG. 4 is an optical tomographic image showing a histological tissue of a pathogen-free seed.
Figure 5:
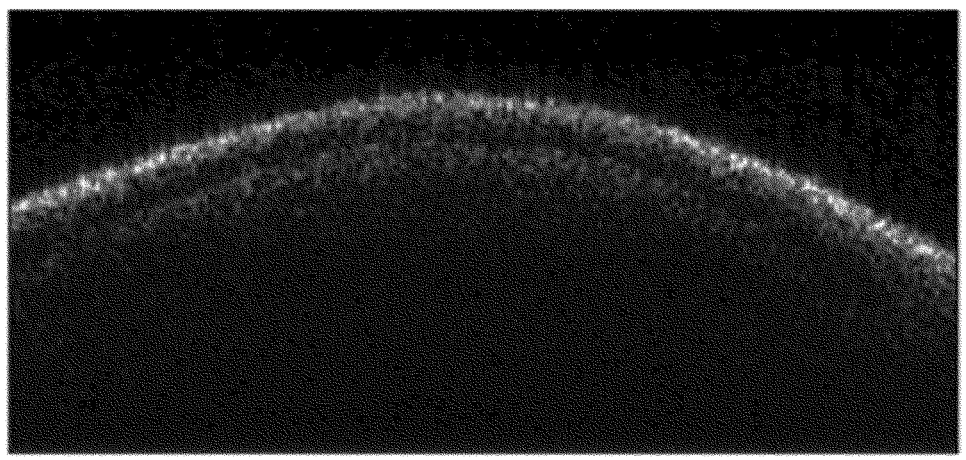
FIG. 5 is an optical tomographic image showing a histological tissue of a pathogen-infected seed.

If there is a discrepancy between the analyzed tomographic image data and the reference tomographic image data, the diagnostic unit 30 diagnoses the seed of interest as a pathogen-infected seed and transmits the diagnosis data indicative of pathogen infection to the selection unit 40 (S160). On the other hand, if there is no discrepancy between them, the diagnostic unit 30 diagnoses the seed of interest as a pathogen-free seed and transmits the diagnosis data indicative of the absence of pathogens to the selection unit 40 (S170). In this context, as shown in FIG. 4, no layers are visualized in the tomographic images. In other words, the reference tomographic image data is already constructed based on this tomographic image of pathogen-free seeds. In contrast, there is a layer in the tomographic image of pathogen-infected seeds as shown in FIG. 5. Accordingly, pathogen-infected seeds can be discriminated from pathogen-free seeds by comparing the tomographic images with the reference.

In the apparatus for non-invasive selection of high-quality seeds, the selection unit 40 is operated according to the diagnosis data transmitted from the diagnostic unit 30 (S180). That is, the selection unit 40 generates selection signals depending on the diagnosis data and orders a separate selection device to sort pathogen-free and pathogen-infected seeds.

The present invention, although described above in the embodiments where seeds are individually scanned by the optical coherence tomographic unit 10, can also be embodied by scanning many seeds collectively. To quote an example, the optical coherence tomographic unit 10 may scan seeds which move in a row at regular intervals of time. When seeds laterally move in a line, the optical coherence tomographic unit 10 may scan all the seeds in one line, e.g., a predetermined number of seeds, simultaneously. In this case, tomographic image data obtained from pathogen-free seeds (high-quality seeds) must only be preset as a reference for the scanning region.

Hence, the diagnostic unit 30 functions to compare the tomographic image data obtained from the scanning region with the present reference tomographic image data to determine whether the images are the same or not. If the images are not coincident with each other, a pathogen-infected seed(s) exists in the seeds of the scanned region. The selection unit 30 can detect pathogen-infected seeds in the seeds of the scanned region by calculating coordinates of the problematic regions in the scanned tomographic image data. Herein, diagnosis of pathogen-infected or pathogen-free seeds, comparison of tomographic image data, and calculation of coordinates may be implemented by operating installed programs, and a detailed description of the program operation is omitted in the embodiments of the present invention.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application.

INDUSTRIAL APPLICABILITY

Based on optical coherence tomography, as described hitherto, the present invention can discriminate pathogen-infected and pathogen-free seeds in a non-invasive manner and thus can screen high-quality seeds with rapidity, convenience, and accuracy at a low cost. Therefore, the present invention is industrially applicable, making a great contribution to agricultural quarantine inspection.

The invention claimed is:

1. An apparatus for non-invasive selection of high-quality seeds, comprising:
    an optical tomographic unit for scanning seeds of diagnostic interest in a non-invasive manner to produce a tomographic image and generating an interference signal of the tomographic image;
    a signal processor for processing the interference signal generated from the optical tomographic unit by performing DC filtering, envelope detection, and digital conversion to generate tomographic image data of the seeds of diagnostic interest;
    a diagnostic unit for determining whether the seeds of diagnostic interest are pathogen-infected seeds or pathogen-free seeds by analyzing tomographic structures of the seeds of diagnostic interest through the tomographic image data generated by the signal processor and comparing the analyzed tomographic image data with preset reference tomographic image data, and for generating diagnosis data, wherein, the diagnostic unit diagnoses the seeds of diagnostic interest as pathogen-infected seeds if there is a layer in the analyzed tomographic structure and if the analyzed tomographic image data and the reference tomographic image data are not coincident with each other, and as pathogen-free seeds if there is no layer in the analyzed tomographic structure and if the tomographic image data generated by the signal processor and the reference tomographic image data are coincident with each other; and
    a selection unit for discriminating pathogen-infected and pathogen-free seeds to select high-quality seeds by sorting out the pathogen-infected seeds from the pathogen-free seeds according to the diagnosis data.

2. The apparatus of claim 1, wherein the interference signal is produced by an optical interferometer in which backscattered light from the seeds of diagnostic seeds and a reference arm of the optical tomographic unit are coupled and converted into an electrical signal so as to allow construction of tomographic images of the seeds.

3. The apparatus of claim 1, wherein the optical tomographic unit comprises:
    a broadband light source for generating a broad band of light for tomography;
    a photocoupler for splitting the light from the light source into two beams and combining the two beams directed backwards;
    a reference arm, connected to the photocoupler, for reflecting the light transmitted from the light source through the photocoupler;
    a sample arm, connected to the photocoupler, for irradiating the seeds of diagnostic interest with the light transmitted from the light source through the photocoupler and for receiving light backscattered from the seeds of diagnostic seed; and
    a photodetector, connected to the photocoupler, for detecting the interference signal of the backscattered light from both the reference arm and the sample arm and for converting the interference signal into an electrical signal.

4. The apparatus of claim 3, wherein the photodetector is a balanced detector having a plus input terminal and a minus input terminal, and the optical tomographic unit further comprises an optical circulator for redirecting a light beam toward the minus terminal of the photodetector, said light beam being redirected back to the broadband light source from the photocoupler.

5. The apparatus of claim 1, wherein when the diagnostic unit diagnoses the seeds as pathogen-free seeds when the analyzed tomographic image data is coincident with the preset reference tomographic image data, the diagnostic unit transmits diagnosis data indicative of absence of pathogens to the selection unit.

6. The apparatus of claim 1, wherein when the diagnostic unit diagnoses the seeds as pathogen-infected seeds when the analyzed tomographic image data is not coincident with the preset reference tomographic image data, the diagnostic unit transmits diagnosis data indicative of pathogen infection to the selection unit.

7. A method for non-invasive selection of high-quality seeds, comprising:
    scanning seeds of diagnostic interest in a non-invasive manner using an optical coherence tomographic unit;
    processing interference signals of the scanned tomographic images by performing DC filtering, envelope detection, and digital conversion to produce tomographic image data of the seeds of diagnostic interest;
    analyzing tomographic structures of the seed of diagnostic interest through the produced tomographic image data;
    comparing the analyzed tomographic image data with preset reference tomographic image data;
    diagnosing the seeds of diagnostic interest to generate diagnosis data, wherein the seeds of diagnostic interest are diagnosed as pathogen-infected seeds if there is a layer in the analyzed tomographic structure and if the analyzed tomographic image data and the reference tomographic image data are not coincident with each other, and as pathogen-free seeds if there is no layer in the analyzed tomographic structure and if the tomographic image data generated by the signal processor and the reference tomographic image data are coincident with each other; and
    selecting high-quality seeds by sorting out the pathogen-infected seeds from the pathogen-free seeds according to the diagnosis data.

8. The method of claim 7, wherein the scanning step comprises:
    generating light from a broadband light source for tomographic scanning of the seeds of diagnostic interest;
    splitting the light coincident from the broadband light source into two light beams and directing the split beams towards a reference arm and a sample arm, respectively;
    reflecting the light, as it is, from the reference arm;

irradiating the seeds of diagnostic interest with the light from the broadband light source and transmitting the backscattered light from the seeds in the sample arm;
coupling the light reflected from both the reference arm and the sample arm; and
converting the coupled light signal into an electric signal to generate an optical interference signal.

* * * * *